US00PP18333P2

(12) United States Plant Patent
Danziger

(10) Patent No.: US PP18,333 P2
(45) Date of Patent: Dec. 18, 2007

(54) *TORENIA* PLANT NAMED 'DANMOON16'

(50) Latin Name: ***Torenia* sp.**
Varietal Denomination: DANMOON16

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 0 days.

(21) Appl. No.: 11/488,599

(22) Filed: Jul. 19, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para
(74) *Attorney, Agent, or Firm*—Foley & Lardner, LLP

(57) ABSTRACT

A new and distinct *Torenia* plant named 'DANMOON16' particularly characterized by plenty of delicate, funnel form, cup-shaped flowers with petals in shades of yellow without a blotch on lower petal; cascading bush, which maintains a compact, rounded plant habit; vigorous growth habit; densely branched plant, gracefully cascading from hanging baskets; early flowering response and stays in full bloom in moderate climate; suitable as an annual for hanging pots outdoors under partial shade; and good weather tolerance with a preferred temperature range of 15° C. to 25° C.

2 Drawing Sheets

Latin name of the genus and species of the plant claimed: *Torenia* sp.
Variety denomination: 'DANMOON16'.

BACKGROUND OF THE INVENTION

The present invention relates to a new and distinct cultivar of *Torenia* plant, botanically known as *Torenia* sp. of the Scrophulariaceae family, and hereinafter referred to by the cultivar name 'DANMOON16'.

The new *Torenia* cultivar is a product of a controlled breeding program conducted by the inventor, Gabriel Danziger, in Moshav Mishmar Hashiva, Israel. The objective of the breeding program was to develop a new *Torenia* cultivar with yellow flowers and cold tolerance.

The new *Torenia* cultivar originated from a cross made by the inventor, Gabriel Danziger, in 2004 in Moshav Mishmar Hashiva, Israel. The female or seed parent is the *Torenia* cultivar designated 'TR-3-1212' (unpatented). The male or pollen parent is the *Torenia* cultivar designated 'TR-1' (unpatented). The new *Torenia* cultivar was discovered and selected by the inventor, Gabriel Danziger, as a single flowering plant within the progeny of the stated cross in a controlled environment in March of 2004 in Moshav Mishmar Hashiva, Israel.

Asexual reproduction of the new *Torenia* cultivar by soft tip cuttings was first performed in June of 2004 in Moshav Mishmar Hashiva, Israel, and has demonstrated that the combination of characteristics as herein disclosed for the new cultivar are firmly fixed and retained through successive generations of asexual reproduction. The new cultivar reproduces true to type.

BRIEF DESCRIPTION OF THE INVENTION

The following traits have been repeatedly observed and are determined to be basic characteristics of 'DANMOON16', which in combination distinguish this *Torenia* as a new and distinct cultivar:

1. Plenty of delicate, funnel form, cup-shaped flowers with petals in shades of yellow without a blotch on lower petal;
2. Cascading bush, which maintains a compact, rounded plant habit;
3. Vigorous growth habit;
3. Densely branched plant, gracefully cascading from hanging baskets;
4. Early flowering response and stays in full bloom in moderate climate;
5. Suitable as an annual for hanging pots outdoors under partial shade; and
6. Good weather tolerance with a preferred temperature range of 15° C. to 25° C.

Plants of the new *Torenia* cultivar 'DANMOON16' differ from plants of the parental cultivars, 'TR-3-1212' and 'TR-1' in the following characteristics described in Table 1.

TABLE 1

| Characteristic | New Cultivar 'DANMOON16' | Female Parent 'TR-3-1212' (unpatented) | Male Parent 'TR-1' (unpatented) |
|---|---|---|---|
| Mature Flower color | Petal shades of yellow, with no blotch on lower petal | Petal shades of orange, with a yellow blotch on lower petal | Petal shades of white, with a yellow blotch on petal |
| Flower size | Depth: About 3.0 cm Width: About 3.2 cm | Depth: About 3.5 cm Width: About 3.2 cm | Depth: About 3.0 cm Width: About 2.5 cm |
| Growth habit | Cascading Bush | Cascading Bush | Bush |
| Flowering Time | 3 weeks from planting | 4 weeks from planting | 2 weeks from planting |

Of the many commercial cultivars known to the present inventor, the most similar in comparison to the new *Torenia* cultivar 'DANMOON16' is the *Torenia* cultivar 'DANTONWHITE', patented, U.S. Plant Pat. No. 16,304 P2. Plants of the new *Torenia* cultivar 'DANMOON16' differ from plants 'DANTONWHITE' in the following characteristics described in Table 2:

TABLE 2

| Characteristic | New Cultivar 'DANMOON16' | Comparison Cultivar 'DANTORWHITE' (PP16,204 P2) |
|---|---|---|
| Mature Flower Color | Petal shades of yellow, with no blotch on lower petal | Petal shades of white, with a yellow blotch on lower petal |
| Flower size | Depth: About 3.0 cm<br>Width: About 3.2 cm | Depth: About 3 cm<br>Width: About 3.5 cm |
| Growth habit | Cascading Bush | Cascading Bush |
| Flowering time | 3 weeks from planting | 8 weeks from planting |

BRIEF DESCRIPTION OF THE PHOTOGRAPHS

The accompanying photographs illustrate the overall appearance of the new *Torenia* cultivar 'DANMOON16' showing the colors as true as is reasonably possible with colored reproductions of this type. Colors in the photographs may differ slightly from the color values cited in the detailed botanical description, which accurately describe the color of 'DANMOON16'.

DETAILED BOTANICAL DESCRIPTION

Figure 1:
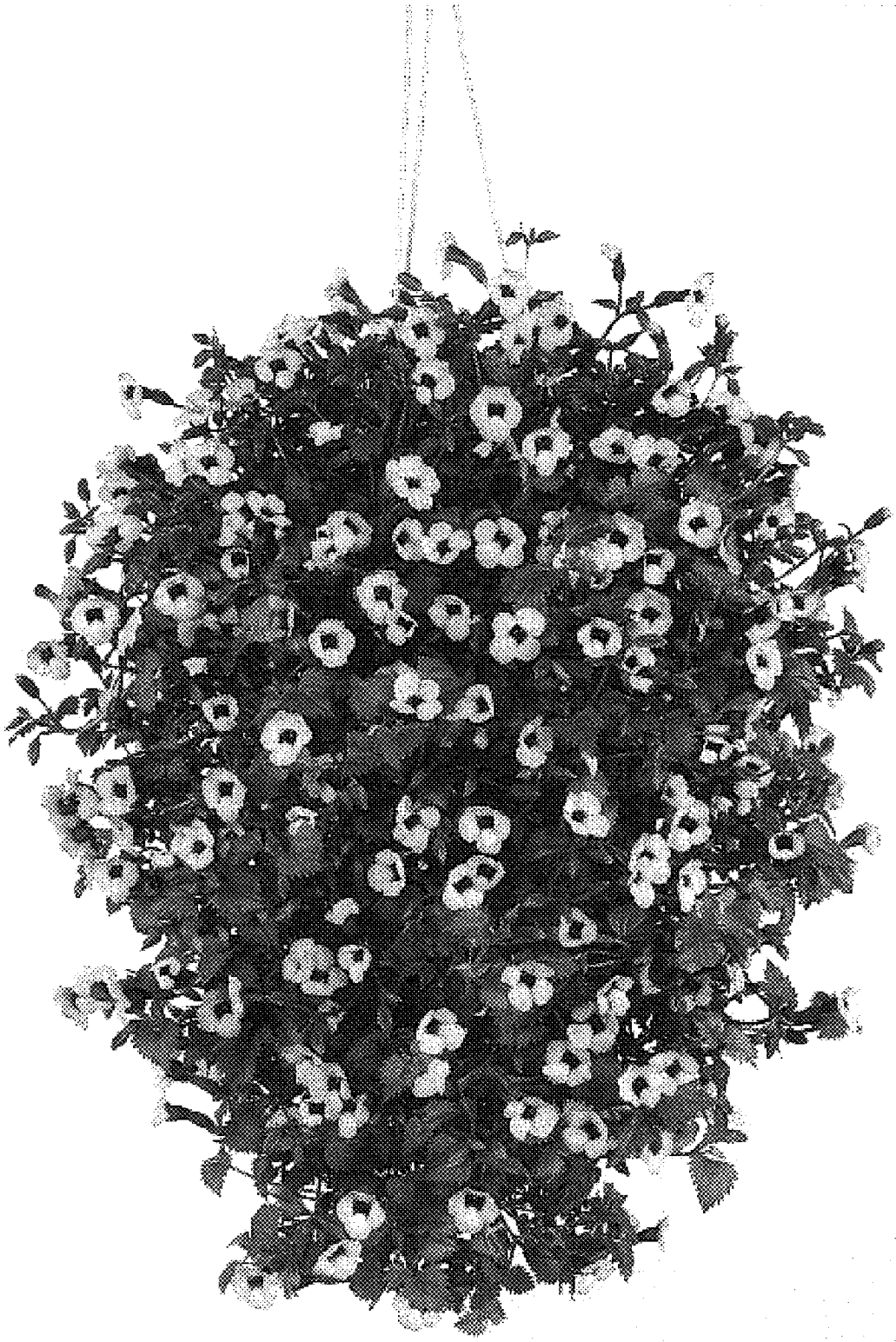
FIG. 1 shows a side perspective view of a typical flowering plant of 'DANMOON16' in a hanging planter at 3 months of age.
Figure 2:
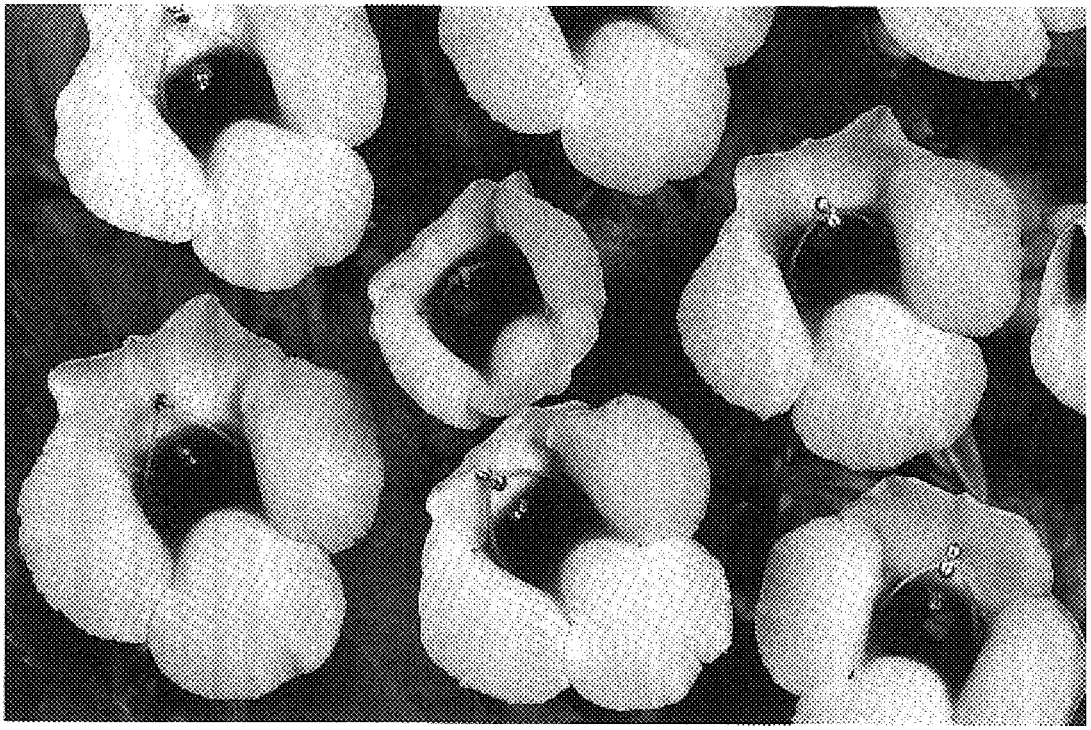
FIG. 2 shows a close-up of the typical flowers, buds and leaves of 'DANMOON16' at 3 months of age.

The new *Torenia* cultivar 'DANMOON16' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'DANMOON16' as grown in a greenhouse in Moshav Mishmar Hashiva, Israel, under conditions which closely approximate those generally used in commercial practice. Optimal growth conditions include that plants of 'DANMOON16' are grown outdoors in a moderate climate and indoors during the winter season. Irrigation and fertilization are recommended on a regular basis. Plants of 'DANMOON16' are usually grown in full sunlight, but partial shade is required in mid summer. Plants of 'Danmoon16' are fully-grown in 3 months from planting a cutting in the summer season and bloom all year-round in a moderate climate. Plants of 'DANMOON16' described herein were grown indoors in 16 cm pots in a glass greenhouse in Moshav Mishmar Hashiva, Israel, with the day temperatures ranging from 18° C. to 35° C. and night temperatures ranging from 16° C. to 25° C. Plants of 'DANMOON16' were fertilized up to a level of 59 ppm N, 35.4 ppm P and 94.4 ppm K.

Color references are made to The Royal Horticultural Society Colour Chart (R.H.S.), 2001 edition, except where general colors of ordinary significance are used. Color values were taken under daylight conditions at approximately noon in Moshav Mishmar Hashiva, Israel. The age of the 'DANMOON16' plants described is 12 weeks.

Parentage:
- *Female or seed parent.*—*Torenia* cultivar designated 'TR-3-1212' (unpatented).
- *Male or pollen parent.*—*Torenia* cultivar designated 'TR-1' (unpatented).

Propagation: Tissue culture and soft tip cuttings.

Plant:
- *Form.*—Bush, cascading.
- *Growth habit.*—Compact, rounded.
- *Height.*—About 10 cm.
- *Spread.*—About 50 cm.
- *Cold tolerance.*—Frost tender. Temperatures below 8° C. may damage plants.
- *Vigor.*—Vigorous growth; plants are fully-grown in 3 months from planting cutting in during summer season.

Stem:
- *Color.*—RHS 146A, yellow-green.
- *Length.*—About 25 cm.
- *Diameter.*—About 3 mm.
- *Pubescence.*—Minimal.
- *Branching.*—About 15 to 30 main branches grow from the base and split into hundreds of secondary and tertiary branches.
- *Length of internodes.*—3.0 cm to 8.5 cm.

Foliage:
- *Overall shape.*—Deltoid.
- *Apex.*—Acute.
- *Base.*—Obtuse.
- *Size of leaf.*—Width: 3.0 cm to 4.0 cm. Length: About 3.5 cm.
- *Margin.*—Serrate.
- *Color.*—Center color of leaf: RHS 137A, green. Upper side: RHS 137A, green. Under side: RHS 146B, yellow-green.
- *Leaf texture.*—Glabrous with sensible veins.
- *Venation.*—Pattern: Anastomotic. Color: Upper surface: RHS 137A, green. Lower surface: RHS 146B, yellow-green.
- *Petioles.*—Length: About 0.8 cm to 1.3 cm. Diameter: About 2 mm. Color: RHS 143A, green.

Flowers:
- *Blooming period.*—All year round in a moderate climate or in a greenhouse environment. In Israel, flowering occurs between February and November outdoors.
- *Flowering response time.*—About 3 weeks from planting.
- *Flowering stem.*—Flowers appear along the growing stems.
- *Quantity of flowers.*—Per stem: About 4 to 7, Per plant: About 200 to 350.
- *Flowering longevity.*—On the plant: about 2 to 5 days, depending on temperature.
- *Type.*—Single.
- *Shape.*—Overall: funnel form; 5-winged. Corolla tube: cylindrical or often broadened above; Corolla: 2-lipped, the upper lip faintly 2-lobed, the lower lip 3-lobed.
- *Orientation at opening.*—Slanted upward.
- *Fragrance.*—None.
- *Flower size.*—Depth: About 3.0 cm. Width: About 3.2 cm.

*Bud.*—Shape: Oblong, cylindrical, ellipsoid, 5-winged. Size: Length: About 2.3 mm. Diameter: About 0.9 mm. Color: Apex: RHS 146A, yellow-green. Base: RHS 146A, yellow-green. Texture: Pubescence on winged edges.

*Floral tube.*—Length: About 3 cm. Width: About 0.3 cm to 1.2 cm. Color: Outside: Primarily purple, RHS N79A, with yellow, RHS 10A (upper side). Inside: Purple, RHS N79B (apex) and RHS N79B (base).

*Petals.*—Number: Four, fused. Length: Upper Petal: About 2.2 cm. Side Petals: About 1.7 cm. Lower Petal: About 1.9 cm. Width: Upper Petal: About 1.3 cm. Side Petals: About 1.1 cm. Lower Petal: About 1.4 cm. Shape: Upper Petal: Overall: orbicular, Apex: rounded, Base: fused. Side Petals: Overall: spatulate, Apex: rounded, Base: fused. Lower: Overall: spatulate, Apex: rounded, Base: fused. Margin: Undulated and toothed. Color: Mature Petals: Upper Surface: Upper, Side & Lower Petals: Entire petal, including margin, RHS 7A, yellow. Lower Surface: Upper, Side & Lower Petals: Entire petal, including margin, RHS 7A, yellow. Throat: Upper throat: RHS N79A, purple. Lower throat: RHS 70B, red-purple. Immature Petals: Upper Surface: Upper, Side & Lower Petals: Entire petal, RHS 7A, yellow. Lower Surface: Upper, Side & Lower Petals: Entire petal, RHS 7A, yellow. Throat: Center of Flower: RHS N79A, purple.

*Sepals.*—Number: 5. Length: About 1.9 cm. Width: About 0.4 cm. Shape: Two-lobed, 5-winged. Apex: Acute. Base: Wedge-shaped. Margin: Undulated. Color: RHS 146A, yellow-green.

*Peduncle.*—Length: About 1 to 3.5 cm. Diameter: About 2 mm. Color: RHS 146A, yellow-green.

Reproductive organs:

*Androecium.*—Stamen: Number: 2 pairs per flower, fused. Color: RHS N80A, purple-violet, and RHS 155C, white. Anther: Length: About 0.4 cm. upper anther shorter — about 0.3 cm. Width: About 0.1 cm. Color: RHS 155C, white. Spur: Present. Filament: Length: About 1 cm; lower filaments are shorter about 0.4 cm. Width: About 0.4 mm. Color: RHS N80A, purple-violet. Pollen: Amount: Moderate. Color: RHS N155A, white. Requirements for pollination: Young flowers, vital pollen, and receptive, open stigma.

*Gynoecium.*—Pistil: Number: One per flower. Length: About 2.9 cm. Stigma: Length: About 0.3 cm. Width: About 0.2 cm. Color: RHS 76A, purple. Style: Length: About 2.4 cm. Color: RHS 75A, purple. Ovary: Number: 1. Length: About 0.5 cm. Width: About 0.2 cm. Color: RHS 144A, yellow-green.

Seed/fruit: None.

Pest/disease resistance and/or susceptibility: A standard preventative spray program is sufficient as no susceptibility was observed.

Temperature tolerance: Sensitive to temperatures below 5° C.

I claim:

1. A new and distinct *Torenia* plant named 'DANMOON16', as illustrated and described herein.

* * * * *